United States Patent [19]
McDonald

[11] Patent Number: 5,395,378
[45] Date of Patent: Mar. 7, 1995

[54] EYE IMPLANTABLE LENS HAPTICS INSERTION AND TWIST APPARATUS

[75] Inventor: Henry H. McDonald, 800 E. Colorado Blvd., Suite 450, Pasadena, Calif. 91101

[73] Assignees: Henry H. McDonald; William W. Haefliger, both of Pasadena, Calif.; a part interest

[21] Appl. No.: 110,185

[22] Filed: Aug. 20, 1993

Related U.S. Application Data

[63] Continuation-in-part of Ser. No. 884,904, May 18, 1992, Pat. No. 5,242,450.

[51] Int. Cl.6 .............................................. A61F 9/00
[52] U.S. Cl. .................... 606/107; 606/205; 623/6
[58] Field of Search ........................... 623/4–6; 606/107, 205, 206, 207, 210, 211

[56] References Cited

U.S. PATENT DOCUMENTS

| | | | |
|---|---|---|---|
| 3,882,872 | 5/1975 | Douvas et al. | |
| 4,190,049 | 2/1980 | Hager et al. | |
| 4,530,117 | 7/1985 | Kelman | 623/6 |
| 4,573,998 | 3/1986 | Mazzocco | 623/6 |
| 4,759,359 | 7/1988 | Willis et al. | 623/6 X |
| 4,813,957 | 3/1989 | McDonald | 623/6 |
| 4,844,065 | 7/1989 | Faulkner | |
| 4,888,015 | 12/1989 | Domino | 623/6 |
| 4,917,680 | 4/1990 | Poley | 623/6 |
| 4,919,130 | 4/1990 | Stoy et al. | 606/107 |
| 4,934,363 | 6/1990 | Smith et al. | 606/107 |
| 4,957,505 | 9/1990 | McDonald | 623/6 |
| 5,047,049 | 9/1991 | Salai | 606/205 |
| 5,098,439 | 3/1992 | Hill et al. | 606/107 |
| 5,147,369 | 9/1992 | Wagner | 606/107 |
| 5,203,789 | 4/1993 | McDonald | 623/6 |
| 5,203,790 | 4/1993 | McDonald | 623/6 |
| 5,217,464 | 6/1993 | McDonald | 606/107 |
| 5,242,450 | 9/1993 | McDonald | 606/107 |

FOREIGN PATENT DOCUMENTS 3305326 8/1984 Germany.
3816059 11/1989 Germany.

*Primary Examiner*—Randall L. Green
*Assistant Examiner*—Mary Beth Jones
*Attorney, Agent, or Firm*—William W. Haefliger

[57] ABSTRACT

Surgical apparatus useful for eye surgery, wherein an incision is made in the eye corneo-scleral tissue, and via which a plastic lens is to be introduced into an eye lens zone in a capsule from which a natural lens has been removed, the lens having haptic structure including haptics attached thereto comprising a surgical forceps having two longitudinally elongated, laterally spaced arms and two blades, the arms extending in parallel relation, each blade integral with an arm at the forward end thereof, each blade being blunt at the forward end thereof; whereby the forceps may be displaced to controllably receive a haptic or lens, or both, between the blades and to controllably displace the haptic or lens, or both, for positioning the haptics and lens in the capsule; and a tube receiving the forceps, with the blades positioned to engage and displace the haptic and lens, in the tube.

10 Claims, 4 Drawing Sheets

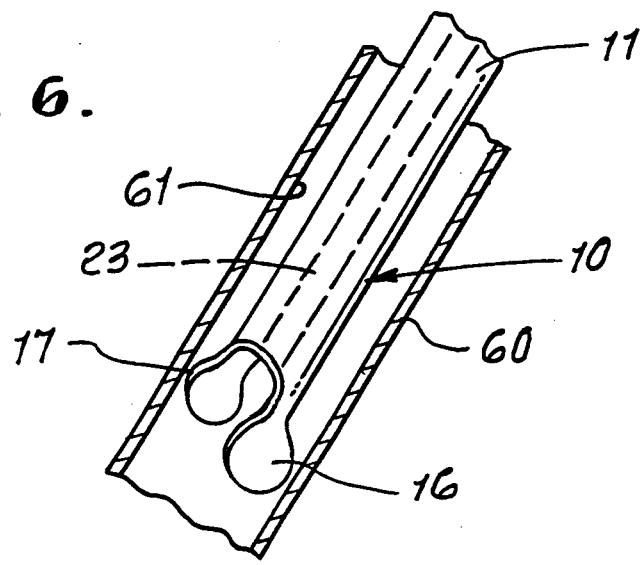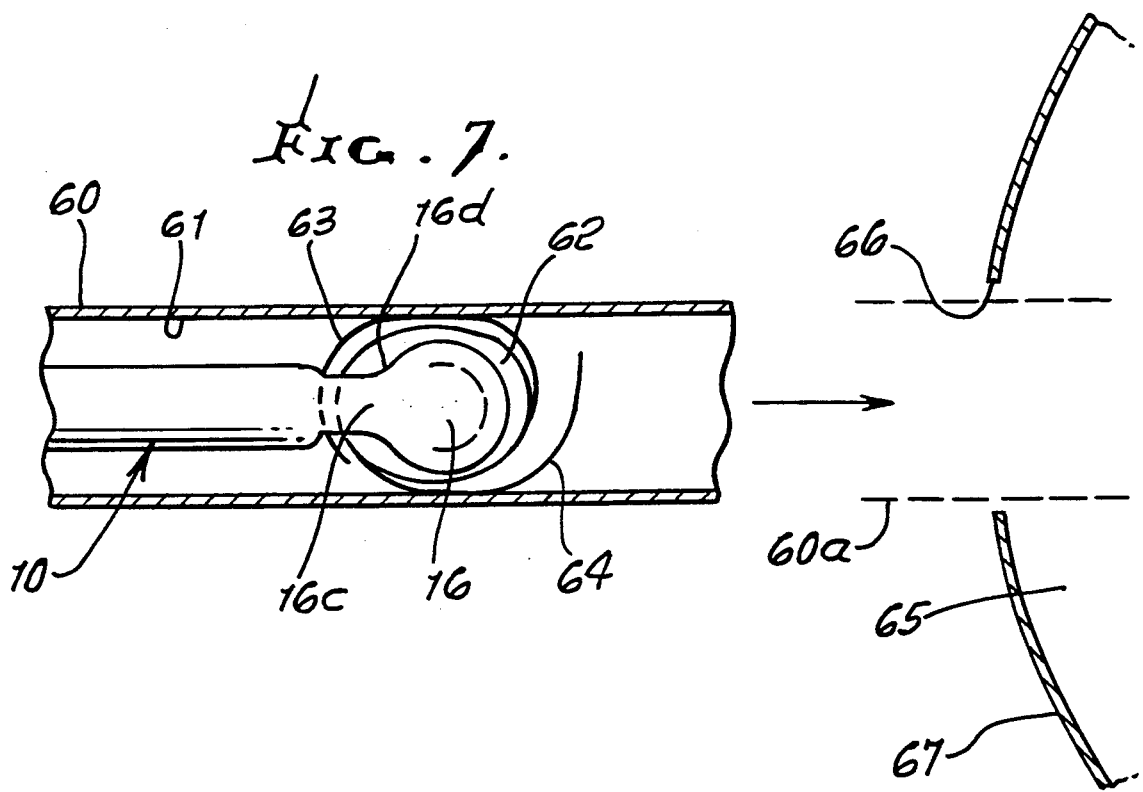

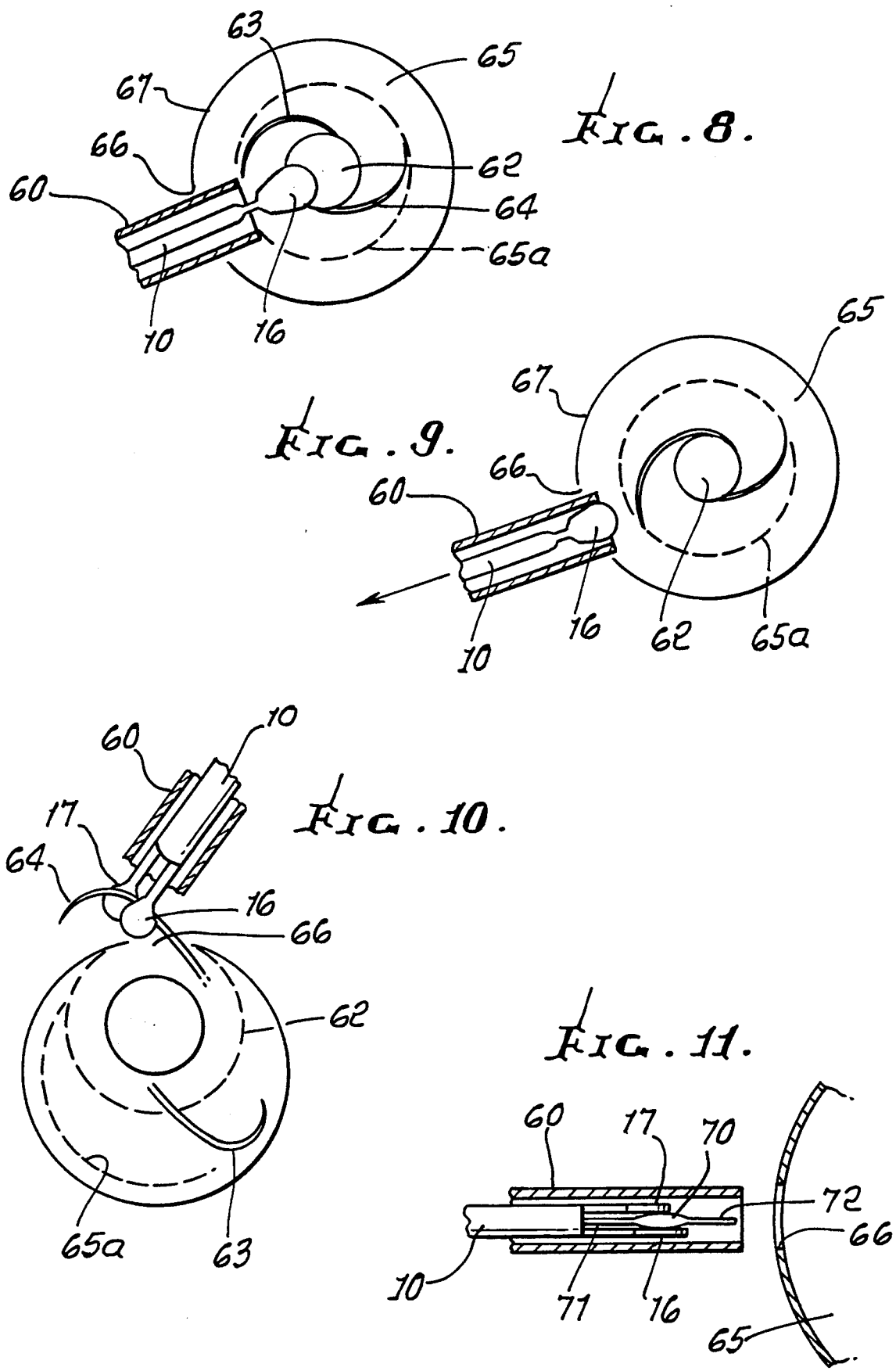

EYE IMPLANTABLE LENS HAPTICS INSERTION AND TWIST APPARATUS

This application is a continuation-in-part of Ser. No. 884,904, filed, May 18, 1992, now U.S. Pat. No. 5,242,450.

BACKGROUND OF THE INVENTION

This invention relates generally to intraocular lens implantation, and more particularly concerns apparatus and method for maneuvering haptics attached to or integral with an artificial lens during its implantation in the eye.

A common difficulty encountered during insertion of an artificial lens into the eye is that of haptic insertion. Generally speaking, two haptics are integral with or attached to or are integral with the lens to project oppositely therefrom; and it is necessary to insert both haptics into the eye cavity in a leading and trailing sequence, as respects the two haptics.

The purpose of the haptics when implanted is to position the lens correctly in the eye. Due to the very short length of the incision in the side wall of the eye, proper maneuvering of the haptics through the incision and into the eye cavity requires great skill. The problem is made more difficult when a folded, soft, silicon lens is to be implanted, since the lens tends to automatically unfold in the eye after its release by forceps, and this can occur suddenly and prior to complete insertion of the lagging or trailing haptic into the eye cavity, disturbing haptic insertion. Thus, failure to achieve the simultaneous insertion of both haptics and lens (i.e., optic) can occur using conventional instrumentation, during cataract surgery. There is, accordingly, great need for improved instrumentation to obviate or minimize this as well as other associated problems.

SUMMARY OF THE INVENTION

It is a major object of the invention to provide improved instrumentation and method for meeting or satisfying the above need. Basically, the surgical apparatus of the invention is useful for eye surgery wherein an incision is made in the eye corneo-scleral tissue, and via which a plastic lens (i.e., implant) is to be introduced into an eye lens zone or capsule from which a natural lens has been removed, the lens having haptic means attached thereto.

Such apparatus comprises, in combination:
 a) a surgical forceps having two longitudinally elongated, laterally spaced arms and two blades, the arms extending in parallel relation, each blade integral with an arm at the forward end thereof, each blade being blunt at the forward end thereof,
 b) whereby the forceps may be displaced to controllably receive a haptic or lens implant, or both, between the blades and to controllably displace the haptic or lens implant, or both, for grasping the haptic, positioning the haptic and lens in the capsule, and releasing same in the eye,
 c) and a guide tube receiving the forceps, with said blades positioned to engage and displace the haptics and lens, in said tube, the tube sized for endwise insertion into the eye via a slit in the eye.

Typically, the forward edge of each blade is bi-directionally forwardly convex, i.e., convex in two planes, as will be described. This assures blade tip bluntness to prevent injury to intraocular tissue. The two blades are located at the distal end of the forceps instrument and can envelop and grasp a haptic or lens implant by rotation of the elongated instrument.

Overt distortion of the haptic or lens implant can occur with upon rotation of the blades, for diverting and steering the haptic into a desired location or locations, such as posteriorly into the sulcus (behind the iris and in front of the lens capsule); or even more posteriorly into the lens capsule "bag" (between the anterior lens capsule and posterior lens capsule). The blades typically have indentations on their sides which help to capture or grasp the haptic or lens implant during instrument rotation, so that the blades do not force the haptic and lens implant away from the grasp of the forceps.

As respects blade tip convexity in two planes, a first such plane extends axially of the instrument and generally normal to the blades to bisect them; and a second axial plane extends normal to the first plane to bisect the space between the blades, whereby:
 i) each blade forward end is forwardly convex in planes parallel to said first plane and intersecting said forward end, and
 ii) each blade forward end is forwardly convex in planes parallel to said second plane and intersecting said forward end.

Also, each blade typically has overall width substantially greater than its thickness.

As respects the provision of indentations on each blade, the blade width may smoothly narrow rearwardly of the blade maximum width zone, all edges of the projected blading being convex or rounded to prevent injury to eye tissue. One blade typically projects forwardly beyond the other, to allow its insertion through the eye slit prior to travel of the shorter blade and grasped haptic through the slit. Also, one blade extends further than the other to allow the shorter blade not to obscure the tip position of the longer blade, enabling accurate placement before rotation of the twister instrument. Grasping of the haptic and lens implant typically occurs inside the eye after saline solution irrigation to deepen the anterior chamber.

It is a further object of the invention to provide the improved forceps with an irrigation cannula extending toward the space between the blades, the cannula having a discharge opening facing that space. The forceps itself may have a generally tubular body to provide the irrigation cannula, and the blades project forwardly from that tubular body.

Yet another object is to provide a method of using the described forceps in conjunction with a tube, the forceps maneuvered in the tube while grasping a haptic, to insert the haptic and lens into the eye.

These and other objects and advantages of the invention, as well as the details of an illustrative embodiment, will be more fully understood from the following specification and drawings, in which:

DRAWING DESCRIPTION

FIG. 6 is a view like FIG. 1 but showing the bladed instrument within a tube insertible into the eye;

FIG. 7 is an enlarged plan view showing the bladed instrument transporting an artificial lens toward a slit in the eye;

FIG. 8 is a view like FIG. 7 showing the bladed instrument expelling the artificial lens in the eye;

FIG. 9 is like FIG. 8 but showing the insertion tube partly retracted;

FIG. 10 is a view showing haptic manipulation after tube retraction; and

FIG. 11 is a view showing a lens having tabular haptics, in a tube and engaged by the bladed instrument.

DETAILED DESCRIPTION

Figure 1:
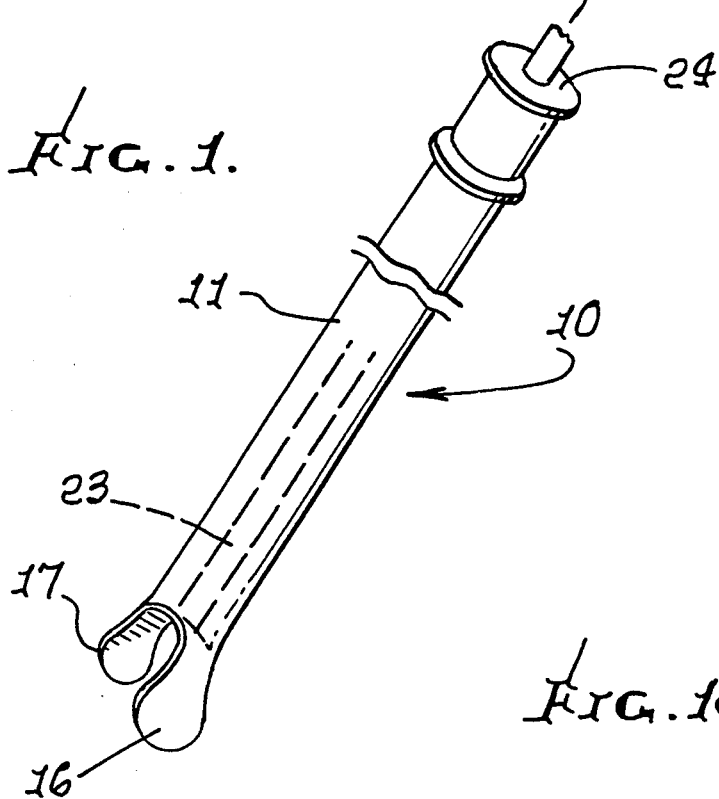
FIG. 1 is a perspective view of an instrument embodying the invention.

In FIGS. 1–4, the surgical forceps 10 has a body 11, which is elongated in the direction 12, the body typically being tubular. The forceps has two longitudinally elongated and laterally spaced arms 13 and 14 which project forwardly from the body and at opposite sides of the body axis 15. These arms extend in generally parallel relation; and arm 14 may be slightly shorter than arm 13 to allow for enhanced capability for grasping and maneuvering of a haptic (typically a trailing haptic as respects insertion into the eye), or trailing edge of a lens implant, or both, by blades carried by the arms, to enable clear viewing of the position of the longer blade (arm) without its being obscured by the shorter blade (arm), and to allow sequential entry of the blades into the eye via a small slit in the sclera. The leading haptic and the lens are typically inserted by use of a forceps or insertion tube.

Figure 2:
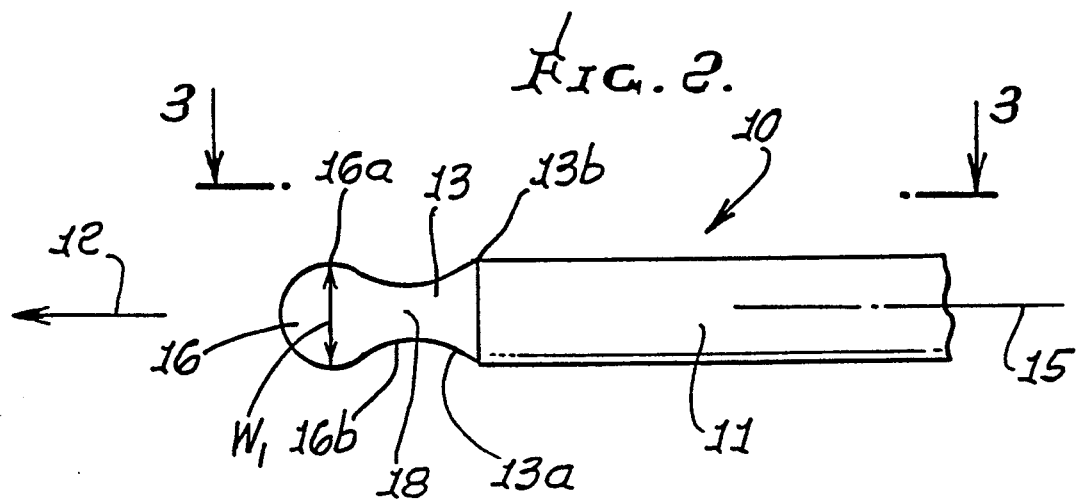
FIG. 2 is a side view of the instrument.
Figure 4:
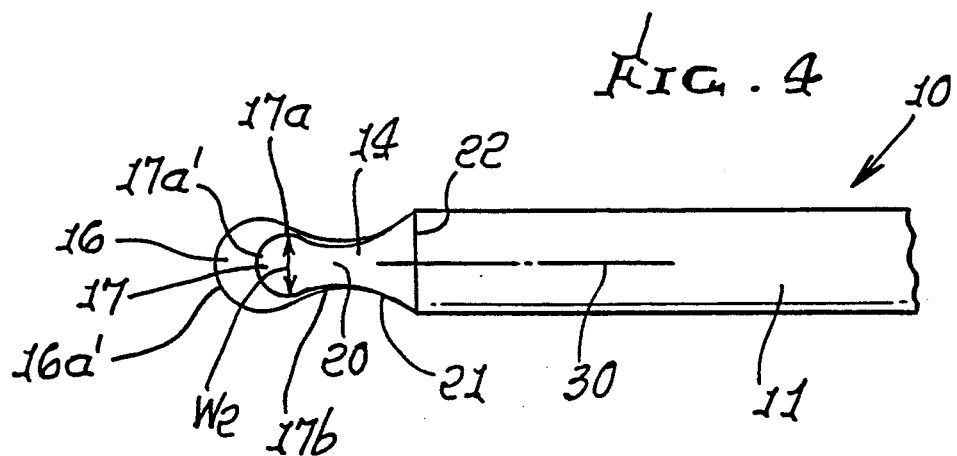
FIG. 4 is a side view of the instrument taken on lines 4—4 of FIG. 3.

Such blades are indicated at 16 and 17 integral with the forward ends of two arms; and they are generally spoon-shaped in outline, as is clear from FIG. 2 and also from FIG. 4. In those FIGS. 2 and 4, each blade is seen to have a width which varies along the length of the blade. Thus, the width $w_1$ of blade 16 increases from the blade tip to a maximum at 16a, and then decreases rearwardly to a minimum at 16b, the blade then joining the arm at region 18, with the arm width increasing at 13a toward juncture with the tube 11 at 13b. In similar fashion, shorter blade 17 has width $w_2$, which increases toward a maximum at 17a and then decreases rearwardly to a minimum at 17b. The blade and arm 14 juncture at 20, with arm 14 width then increasing rearwardly along concave edges 21 to merge with the tube 11 at points 22.

In FIG. 4, it is clear that blade 16 projects forwardly to greater extent than blade 17, the latter being slightly smaller in outline than blade 16, enhancing the haptic maneuvering functions and capability of the two blades, and also enabling one blade to precede the other into the narrow slit in the sclera.

The body 11 provides a cannula 23, which is elongated from the rearward end of the instrument 24 and which discharges openly at 25 between the two arms 13 and 14, whereby liquid, such as a saline aqueous solution, may be supplied during surgery to discharge onto and into the eye to prevent collapse of the eye "bag" during haptic and lens insertion maneuvering, as referred to. See saline solution supply at 40 and duct 41.

Figure 1A:
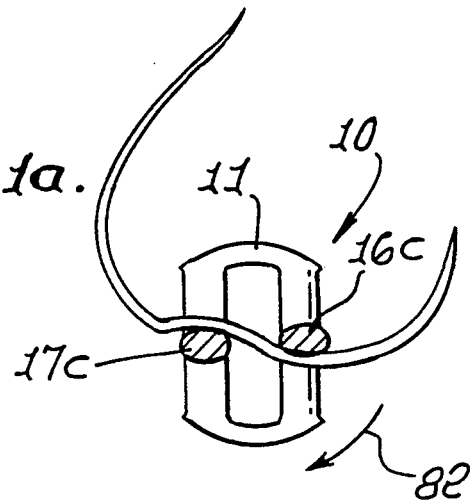
FIG. 1a is an enlarged fragmentary section showing haptic strand capture by twisting blades.
Figure 5:
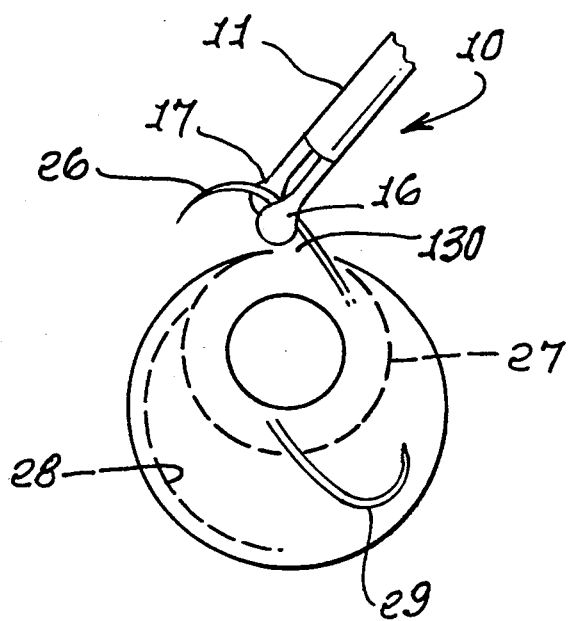
FIG. 5 is a front view of an eye iris and pupil, with a folded lens being implanted, the lens having become unfolded and the trailing haptic being maneuvered into the eye cavity by the instrument of the invention, the trailing edge of the lens implant also being maneuverable.

In FIG. 5 and FIG. 1a, the instrument 10 is shown with the two blades on blade arms, grasping the trailing haptic trailing portion 26, which is shown projecting outwardly from the eye during insertion. The lobe-shaped blades have been positioned beyond the haptic strand so that the strand is between the narrowed blade portions 16c and 17c. See FIG. 1a. The instrument is then twisted or rotated about its axis 15 (as in direction 82 in FIG. 1a) to "capture" the haptic strand between the narrowed portions of the blades, as also indicated in FIG. 1 and also in FIG. 1a. The direction of twist is shown at 28 in FIG. 1a.

In addition, the narrowing of the blade arm extents between which the haptic is captured locates the captured haptic lengthwise of the instrument to prevent it from sliding endwise off the instrument so long as the instrument is twisted, as described. This then enables the surgeon to implant the trailing haptic or lens implant, or both, into the eye cavity via the narrow slit in the wall of the eye, as referred to. See in this regard the slit 30 shown in FIG. 5, lens 27 that has passed through the slit into the eye bag 28, and opened (if folded) and the leading haptic 25 in the eye. Bi-directional bluntness or convexity of blade edges assures that eye tissue will not be damaged by push contact with the blades during haptic twisting and insertion via the slit into the eye.

As regards blade bi-directional edge convexity, note a first axial plane 30 extending generally normal to the blades in FIG. 4, and a second axial plane 31 extending generally normal to plane 30 and bisecting the space (see FIG. 2). Having such planes defined, the following convexities exist:

i) each blade forward end (see ends 16a and 17a) is forwardly convex in planes parallel to the first plane 30 (see convexities at ends 16a and 17a in FIG. 3), and ii) each blade forward end is forwardly convex in planes parallel to the second plane 32 and intersecting the blade forward end (see convexities at ends 16a' and 17a' in FIG. 4).

Figure 3:
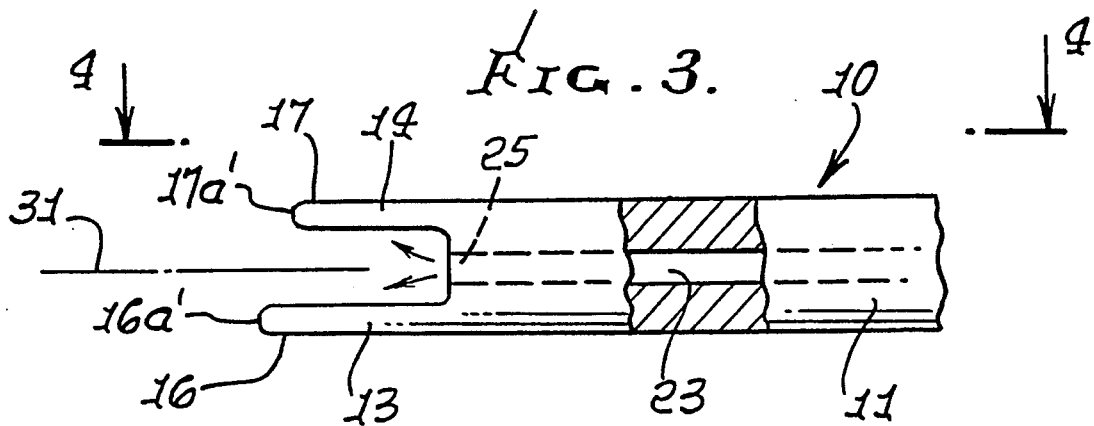
FIG. 3 is a side view of the instrument taken on lines 3—3 of FIG. 2.

Also, each blade has overall width substantially greater than the blade thickness, as is clear from FIGS. 3 and 4.

The instrument is also usable to force the haptic or lens implant, or both, to be released in the sulcus, posterior to the iris; and to grasp a displaced (luxated or sub-luxated) haptic lens optic which has inadvertently fallen into the depths of the eye, for retrieval without severe damage to the intraocular tissues and positioning of the haptic lens optic for a very satisfactory intro-capsular implantation.

Referring to FIG. 6, a view similar to FIG. 1, the forceps apparatus 10 is shown extending within a tube 60 having a bore 61, as also seen in FIG. 7. In the latter view, the forceps is shown gripping or holding a lens 62 having haptics 63 and 64 confined in the tube. Note haptic 63 retained between narrowed blade portions 16c and 17c. The haptics typically engage the tube bore 61 providing stability of lens positioning in the tube. The tube is insertible into the eye region 65 via a slit 66 formed in a wall 67 of the eye. See the broken line position 60a of the tube forward end in FIG. 7. The forceps 10 carrying the lens is then displaced forwardly in the tube into the eye to release the lens, as for example in response to leftward twisting of the forceps. Initial gripping of the lens or its haptic or haptics is accomplished by rightward twisting of the forceps, including its blades. Note the abrupt angulations at 16d between the blade 16 and the narrowed stem 16c, to enhance grasping of the haptic or lens implant edge. Both blades may have such abrupt angulation.

FIG. 8 is another view showing insertion of the tube through the slit in the eye wall, the lens then being movable forwardly by the forceps blades into the capsule designated at 65a for release. Note the haptic 64, which has been released, to expand into the position shown to engage the internal periphery of the capsule for ultimate positioning of the lens 62.

FIG. 9 is a view showing the retraction of the tube 60 after the lens and the haptics have been released by the forceps within the eye capsule. Note that the tube enables controlled twisting of the forceps both to the right and to the left, to enable controlled gripping and releasing of the lens 62 into the eye bag 65a.

FIG. 10 shows the use of the forceps blades 16 and 17 to maneuver the haptic 64 through the slit 66, if need be and into the capsule, the tube 60 at this time being located to project outside or into the eye region about the capsule. The tube directs and steadies the forceps, which can be moved lengthwise relative to the tube and rotated therein to maneuver the haptic 64 into the bag 65a.

In FIG. 7, the haptics 63 and 64 may engage the bore 61 of the tube with light friction to enable twisting of the forceps relative to the lens, for controlled twisting, as referred to, the narrowing of the blades at 16b and 17b, as described above, contributing to these functions and the desired results in terms of a lens gripping and lens release at precise times desired by the physician.

FIG. 11 shows gripping by the blades 16 and 17 of a lens 70 having tabular haptics 71 and 72, and within the tube 60, as referred to, for controlled insertion and release in the eye, indicated at 65.

The method of maneuvering a lens haptic or lens implant into desired position in the eye includes the steps:
a) providing a tube to be partly inserted endwise in the eye,
b) providing bladed means, and stem therefore, in the tube,
c) causing the tube to enter the eye and causing the bladed means to engage the haptic or lens implant edge and eject the haptic and lens from the tube and into the eye,
d) causing the bladed means to grasp the haptic or lens implant by twisting the stem in the tube to twist the bladed means to effect displacement of the haptic or implant adjacent the bladed means,
e) and maneuvering the grasped haptic or lens implant into desired position in the eye by maneuvering the stem in the tube.

That method also includes irrigating the grasped haptic or lens implant during said maneuvering.

Haptic release after completed positioning includes reverse twisting of the blade means, and withdrawal of the blade means from the eye, via the slit in the sclera. That slit is typically between 3 and 4 millimeters in length, so that the overall diameter of the instrument 10 is typically between 3 and 6 millimeters.

Additional steps include irrigating the grasped haptic during maneuvering; and releasing the grasped haptic in the eye by reverse twisting of the stem in the tube and of the bladed means forwardly of the tube.

In the above, the forceps and its blades cut as a piston to push the lens from the tube, the bluntness of the blades assuring absence of damage to the lens and haptics.

I claim:
1. Surgical apparatus useful for eye surgery, wherein an incision is made in the eye corneo-scleral tissue, and via which a plastic lens is to be introduced into an eye lens zone in a capsule from which a natural lens has been removed, the lens having haptic means including haptics attached thereto, the combination comprising:
   a) a surgical forceps having two longitudinally elongated, laterally spaced arms and two spaced blades, said arms extending in parallel relation, each blade integral with an arm at a forward end thereof, each blade being blunt at a forward end of said blade,
   b) whereby the forceps may be displaced to controllably receive a haptic or lens between the blades and to controllably displace the haptic or lens for positioning the haptic and lens in said capsule,
   c) and a tube receiving the forceps, with said blades positioned to engage and displace the haptics and lens, in said tube,
   d) each blade forward end being forwardly convex, in parallel planes, each blade having width that narrows rearwardly of said blade forward end, each blade having maximum width forward of said narrowed width substantially less than a bore defined by the tube, providing clearance to receive said haptic means.
2. The combination of claim 1 wherein each blade forward end is bi-directionally forwardly convex.
3. The combination of claim 1 wherein each blade has thickness, the forceps defining a longitudinally forwardly extending axis located midway between the blades, there being a first axial plane extending generally normal to said blades and bisecting the blades, and there being a second axial plane extending normal to said first plane and bisecting a space between the blades, and
   i) each blade forward end being forwardly convex in planes parallel to said first plane and intersecting said blade forward end, and
   ii) each blade forward end being forwardly convex in planes parallel to said second plane and intersecting said blade forward end.
4. The combination of claim 2 wherein the narrowest width of each blade is substantially greater than said blade thickness.
5. The combination of claim 1 wherein the forceps includes an irrigation cannula extending toward the space between said blades, the cannula having a discharge opening facing said space.
6. The combination of claim 3 wherein the forceps includes an irrigation cannula extending toward the space between said blades, the cannula having a discharge opening facing said space.
7. The combination of claim 1 wherein the forceps have a generally tubular body from which said arms project forwardly.
8. The combination of claim 6 wherein the forceps have a generally tubular body from which said arms project forwardly, and said tubular body forming said cannula.
9. The combination of claim 1 wherein the tube has an open forward end to be inserted into the eye via a slit therein, the forceps arms extending toward said open end to eject the lens and haptics into said eye.
10. Surgical apparatus useful for eye surgery, wherein an incision is made in the eye corneo-scleral tissue, and via which a plastic lens is to be introduced into any eye lens zone in a capsule from which a natural lens has been removed, the lens having haptics attached thereto, the combination comprising:

a) a surgical forceps having two longitudinally elongated, laterally spaced arms and two spaced blades, said arms extending in parallel relation, each blade having integral connection with one of said arms at a forward end of said arm, each blade being blunt at a forward end of said blade, b) whereby the forceps may be displaced to controllably receive a haptic or the lens between the blades and to controllably bend the haptic or lens for positioning the haptic and lens in said capsule, c) each blade having width and thickness, the forceps defining a longitudinally forwardly extending axis located midway between the blades, there being a first axial plane extending generally normal to said blades and widthwise bisecting the blades, and there being a second axial plane extending normal to said first plane and bisecting the space between the blades, and i) each blade forward end being forwardly convex in planes parallel to said first plane and intersecting said blade forward end, and ii) each blade forward end being forwardly convex in planes parallel to said second plane and intersecting said blade forward end, the blade width narrowing rearwardly of said blade forward end, each blade being oval in outline in planes parallel to said second plane, d) the forceps having a generally tubular body from which said arms project forwardly, said tubular body forming an irrigation cannula extending toward the space between the blades, the cannula having a discharge opening facing said space, e) and a tube receiving the forceps, with said blades positioned to engage and displace the haptics and lens, in said tube, with clearance between the blades and tube to receive the haptics.

* * * * *